(12) United States Patent
Wright

(10) Patent No.: US 6,277,788 B1
(45) Date of Patent: Aug. 21, 2001

(54) HIGHLY CONCENTRATED AQUEOUS GLYPHOSATE COMPOSITIONS

(75) Inventor: Daniel R. Wright, St. Louis, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/444,768

(22) Filed: Nov. 22, 1999

Related U.S. Application Data

(60) Provisional application No. 60/109,532, filed on Nov. 23, 1998.

(51) Int. Cl.$^7$ .................................................. A01N 57/02
(52) U.S. Cl. .............................................................. 504/206
(58) Field of Search ............................................... 504/206

(56) References Cited

U.S. PATENT DOCUMENTS

| | | | |
|---|---|---|---|
| 3,799,758 | 3/1974 | Franz | 71/86 |
| 3,853,530 | 12/1974 | Franz | 71/76 |
| 3,977,860 | 8/1976 | Franz | 71/86 |
| 4,140,513 | 2/1979 | Prill | 71/86 |
| 4,315,765 | 2/1982 | Large | 71/87 |
| 4,405,531 | 9/1983 | Franz | 260/501.12 |
| 4,481,026 | 11/1984 | Prisbylla | 71/86 |
| 4,507,250 | 3/1985 | Bakel | 260/502.5 F |
| 5,118,444 | 6/1992 | Nguyen | 252/390 |
| 5,317,003 | 5/1994 | Kassebaum et al. | 504/116 |
| 5,389,598 | 2/1995 | Bert et al. | 504/206 |
| 5,464,807 | 11/1995 | Claude et al. | 504/206 |
| 5,652,197 | 7/1997 | Claude et al. | 504/206 |
| 5,668,085 | 9/1997 | Forbes et al. | 504/206 |
| 5,703,015 | 12/1997 | Berger et al. | 504/206 |
| 5,750,468 | 5/1998 | Wright et al. | 504/206 |
| 5,888,934 | * 3/1999 | Townson et al. | 504/206 |
| 6,040,272 | * 3/2000 | Riego et al. | 504/206 |

FOREIGN PATENT DOCUMENTS

| | | | |
|---|---|---|---|
| 0 274 369 | 7/1988 | (EP) | A01N/57/20 |
| 0 364 202 | 4/1990 | (EP) | A01M/57/20 |
| 1 588 079 | 4/1981 | (GB) | C07C/93/04 |
| 95/33379 | 12/1995 | (WO) | A01N/33/04 |
| 97/16969 | 5/1997 | (WO) | A01N/25/30 |
| 97/32476 | 9/1997 | (WO) | A01N/25/30 |
| 98/17109 | 4/1998 | (WO) | A01N/25/30 |
| 98/33384 | 8/1998 | (WO) | A01N/57/20 |
| 98/33385 | 8/1998 | (WO) | A01N/57/20 |
| WO99/59407 | 11/1999 | (WO) | A01N/25/34 |

OTHER PUBLICATIONS

Wyrill & Burnside: Glyphosate toxcity to common milkweed and hemp dogbane as influenced by surfactants. Weed Science 25, 275–287 (1977).

* cited by examiner

*Primary Examiner*—S. Mark Clardy
(74) *Attorney, Agent, or Firm*—Senniger, Powers, Leavitt & Roedel; Joseph A. Schaper; James C. Forbes

(57) ABSTRACT

A herbicidal composition is provided comprising an aqueous solution of N-phosphonomethylglycine, predominantly in the form of the monoethanolammonium salt thereof, at a concentration of about 30% to about 48% N-phosphonomethylglycine acid equivalent by weight. In a particular embodiment, a herbicidal composition comprises water; N-phosphonomethylglycine predominantly in the form of the monoethanolammonium salt thereof in solution in the water in an amount of about 360 to about 570 g a.e./l of the composition; and a surfactant component in solution or stable dispersion in the water, comprising one or more surfactants in a total amount of about 20 to about 200 g/l of the composition, this surfactant component being selected such that the composition has a cloud point not lower than about 50° C.

20 Claims, 1 Drawing Sheet

HIGHLY CONCENTRATED AQUEOUS GLYPHOSATE COMPOSITIONS

This application claims the benefit of U.S. provisional application Ser. No. 60/109,532 filed Nov. 23, 1998.

FIELD OF THE INVENTION

The present invention relates to herbicidal compositions useful in agriculture and related industries. More specifically, the present invention relates to aqueous concentrate compositions containing as active ingredient a salt of the herbicide glyphosate (N-phosphonomethylglycine), and to a method of killing or controlling unwanted vegetation using such compositions.

BACKGROUND OF THE INVENTION

Glyphosate is well known in the art as an effective post-emergent foliar-applied herbicide. In its acid form, glyphosate has a structure represented by formula (I):

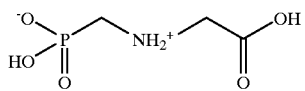

(I)

and is relatively insoluble in water (1.16% by weight at 25° C.). For this reason it is typically formulated as a water-soluble salt.

Monobasic, dibasic and tribasic salts of glyphosate can be made. However, it is generally preferred to formulate glyphosate and apply glyphosate to plants in the form of a monobasic salt. The most widely used salt of glyphosate is the mono(isopropylammonium), often abbreviated to IPA, salt. Commercial herbicides of Monsanto Company having the IPA salt of glyphosate as active ingredient include Roundup®, Roundup® Ultra, Roundup® Xtra and Rodeo® herbicides. All of these are aqueous solution concentrate (SL) formulations and are generally diluted in water by the user prior to application to plant foliage. Other glyphosate salts which have been commercially formulated as SL formulations include the mono(trimethylsulfonium), often abbreviated to TMS, salt, used for example in Touchdown® herbicide of Zeneca.

Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

Among the water soluble salts of glyphosate known in the literature, but never used commercially before the priority filing date hereof, is the monoethanolammonium (MEA) salt, having a structure represented by formula (II):

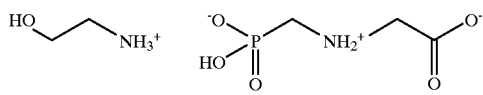

(II)

in the ionic form predominantly present in aqueous solution at a pH of about 4. This salt is disclosed, for example, by Franz in U.S. Pat. No. 4,405,531 cited above, as one of a very long list of organic ammonium salts of glyphosate useful as herbicides, and, as an example of a monoalkanolammonium salt, is included among the "particularly preferred" compounds disclosed therein. An aqueous solution of the MEA salt of glyphosate can be prepared by reacting approximately equimolar amounts of glyphosate acid and monoethanolamine in an aqueous medium. The reaction is exothermic.

Very few herbicides have been commercialized as their MEA salts. Clopyralid (3,6-dichloro-2-pyridinecarboxylic acid) is formulated as its MEA salt in certain herbicide products sold by DowElanco under the trademark Lontrel®.

Glyphosate MEA salt has a molecular weight of 230, very similar to that of glyphosate IPA salt (228).

Solubility of glyphosate MEA salt in water is believed not to be recorded in prior art but is readily determined by procedures familiar to those skilled in the art. Similarly, aqueous solutions of glyphosate MEA salt at concentrations greater than about 40% by weight are believed not to have been specifically disclosed, thus any unusual or unpredicted properties of such solutions have not been publicly known. Concentrations expressed as percent by weight herein relate to parts by weight of salt or acid equivalent per 100 parts by weight of solution.

It can now be disclosed that glyphosate MEA salt has been determined to have a solubility in pure water at 20° C. of about 64% by weight, that is, about 47% glyphosate acid equivalent (a.e.) by weight. This is very similar to the solubility of the IPA salt. Thus a simple aqueous solution concentrate of glyphosate MEA salt can readily be provided at a concentration of, for example, 46% a.e. by weight, comparable to that commercially obtainable with glyphosate IPA salt, as in the aqueous solution concentrate available from Monsanto Company under the name MON 0139.

A major advantage of the IPA salt over many other salts of glyphosate has been the good compatibility in aqueous solution concentrate formulations of that salt with a wide range of surfactants. Glyphosate salts generally require the presence of a suitable surfactant for best herbicidal performance. The surfactant can be provided in the concentrate formulation, or it can be added by the end user to the diluted spray composition. The choice of surfactant has a major bearing on herbicidal performance. For example, in an extensive study reported in Weed Science, 1977, volume 25, pages 275–287, Wyrill and Burnside found wide variation among surfactants in their ability to enhance the herbicidal efficacy of glyphosate, applied as the IPA salt.

Beyond some broad generalizations, the relative ability of different surfactants to enhance the herbicidal effectiveness of glyphosate is highly unpredictable.

Surfactants tending to give the most useful enhancement of glyphosate herbicidal effectiveness are generally but not exclusively cationic surfactants, including surfactants which form cations in aqueous solution or dispersion at pH levels of around 4–5 characteristic of SL formulations of monobasic salts of glyphosate. Examples are long-chain (typically $C_{12}$ to $C_{18}$) tertiary alkylamine surfactants and quaternary alkylammonium surfactants. The term "alkyl" as conventionally used herein in describing surfactant structures includes unsaturated as well as saturated hydrocarbyl chains. An especially common tertiary alkylamine surfactant used in aqueous solution concentrate formulations of glyphosate IPA salt has been the very hydrophilic surfactant polyoxyethylene (15) tallowamine, i.e., tallowamine having in total about 15 moles of ethylene oxide in two polymerized ethylene oxide chains attached to the amine group as shown in formula (III):

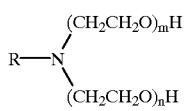

(III)

where R is a mixture of predominantly $C_{16}$ and $C_{18}$ alkyl and alkenyl chains derived from tallow and the total of m+n is an average number of about 15.

For certain applications, it has been found desirable to use a somewhat less hydrophilic alkylamine surfactant, such as one having less than about 10 moles of ethylene oxide, as suggested in U.S. Pat. No. 5,668,085 to Forbes et al., for example polyoxyethylene (2) cocoamine. That patent discloses illustrative aqueous compositions comprising such a surfactant together with the IPA, ammonium or potassium salts of glyphosate.

A wide variety of quaternary ammonium surfactants have been disclosed as components of aqueous solution concentrate formulations of glyphosate IPA salt. Illustrative examples are polyoxyethylene (2) cocoammonium chloride, disclosed in European Patent No. 0 274 369, polyoxyethylene (15) cocoammonium chloride, disclosed in U.S. Pat. No. 5,317,003, and various quaternary ammonium compounds having formula (IV):

(IV)

where $R^1$, $R^2$ and $R^3$ are each $C_{1-3}$ alkyl groups and n is an average number from 2 to 20, disclosed in U.S. Pat. No. 5,464,807.

PCT Publication No. WO 97/16969 discloses aqueous solution concentrate compositions of glyphosate, in the form of the IPA, methylammonium and diammonium salts, comprising a quaternary ammonium surfactant and an acid salt of a primary, secondary or tertiary alkylamine compound.

Other cationic surfactants which have been indicated as useful in aqueous solution concentrate compositions of glyphosate salts include those disclosed in PCT Publication No. WO 95/33379. It is further disclosed in PCT Publication No. WO 97/32476 that highly concentrated aqueous compositions of glyphosate salts can be made with certain of these same cationic surfactants, with the further addition of a defined component that enhances stability of the compositions. Glyphosate salts exemplified therein are the IPA salt and the mono- and diammonium salts.

Among amphoteric or zwitterionic surfactants reported to be useful components of aqueous solution concentrate formulations of glyphosate IPA salt are alkylamine oxides such as polyoxyethylene (10-20) tallowamine oxide, disclosed in U.S. Pat. No. 5,118,444.

Nonionic surfactants are generally reported to be less effective in enhancing herbicidal activity than cationic or amphoteric surfactants when used as the sole surfactant component of SL formulations of glyphosate IPA salt; exceptions appear to include certain alkyl polyglucosides, as disclosed for example in Australian Patent No. 627503, and polyoxyethylene (10-100) $C_{16-22}$ alkylethers, as disclosed in PCT Publication No. WO 98/17109. Anionic surfactants, except in combination with cationic surfactants as disclosed in U.S. Pat. No. 5,389,598 and U.S. Pat. No. 5,703,015, are generally of little interest in SL formulations of glyphosate IPA salt.

Although some of the surfactant types mentioned above have been disclosed as being useful in compositions of glyphosate salts in general, none of them has been specifically disclosed in association with glyphosate MEA salt. Recently, a class of alkyletheramine, alkyletherammonium salt and alkyletheramine oxide surfactants has been disclosed in U.S. Pat. No. 5,750,468 to be suitable for preparation of aqueous solution concentrate formulations of various glyphosate salts, the MEA salt being included in the list of salts mentioned. It is disclosed therein, without reference to any particular glyphosate salt, that an advantage of the subject surfactants when used in an aqueous composition with glyphosate salts is that these surfactants permit the glyphosate concentration of the composition to be increased to very high levels. There is no suggestion, however, of any particular advantage in this regard when the glyphosate salt used is the MEA salt.

It is likely that serious consideration of glyphosate MEA salt as a herbicidal active ingredient has been inhibited hitherto by relative difficulty in formulating this salt as a highly concentrated SL product together with preferred surfactant types. As illustration of the problems involved in formulating glyphosate MEA salt with surfactants, the hitherto most widely used surfactant in glyphosate IPA salt compositions, namely polyoxyethylene (15) tallowamine of formula (III) above, is relatively incompatible in aqueous solution with glyphosate MEA salt.

For example, one convenient and practically useful indicator of surfactant/salt compatibility in concentrated aqueous solutions is "cloud point". This is a measure of the maximum temperature at which a given aqueous composition containing a surfactant and a salt at defined concentrations forms a single-phase solution. Above the cloud point, the surfactant separates from the solution, initially as a hazy or cloudy dispersion, and, upon standing, as a distinct phase generally rising to the surface of the solution. Cloud point of a composition is normally determined by heating the composition until the solution becomes cloudy, and then allowing the composition to cool, with agitation, while its temperature is continuously monitored. A temperature reading taken when the solution clears is a measure of cloud point.

A cloud point of 50° C. or higher is normally considered acceptable for most commercial purposes for a glyphosate SL formulation. As shown in Table 1 below, an aqueous solution of glyphosate IPA salt at a concentration of 31% a.e. by weight can be loaded with up to 15% by weight of polyoxyethylene (15) tallowamine while maintaining a cloud point of 50° C. or higher, whereas an aqueous solution of glyphosate MEA salt at the same a.e. concentration can tolerate only up to 4% by weight of the same surfactant without the cloud point falling significantly below 50° C. At 8% or more by weight of polyoxyethylene (15) tallowamine, the surfactant is insoluble in a 31% a.e. by weight aqueous solution of glyphosate MEA salt, even at room temperature (20–25° C.). A surfactant loading of 4% or lower in a concentrate composition having a glyphosate concentration of 31% a.e. by weight or higher is unlikely to provide the herbicidal effectiveness sought by the glyphosate herbicide user, except in situations where the herbicide is to be applied in an extremely low water volume such that a surfactant concentration of about 0.1% or higher is maintained in the diluted application composition.

TABLE 1

Cloud points of glyphosate salt solutions containing polyoxyethylene (15) tallowamine surfactant[1] at various concentrations

| Surfactant concentration (wt %) | Cloud point (° C.) IPA salt, 31 wt % a.e. | Cloud point (° C.) MEA salt, 31 wt % a.e. |
|---|---|---|
| 2 | 88 | 67 |
| 4 | 84 | 49 |
| 6 | 79 | 45 |
| 8 | 75 | insoluble at 20–25° C. |
| 10 | 70 | insoluble at 20–25° C. |
| 15 | 50 | insoluble at 20–25° C. |
| 20 | 40 | insoluble at 20–25° C. |

[1]Ethomeen ™ T/25 of Akzo

At glyphosate a.e. concentrations higher than 31% a.e. by weight, the amount of polyoxyethylene (15) tallowamine that can be included in a composition while maintaining an acceptably high cloud point is even lower.

It would be desirable to provide a storage-stable aqueous solution concentrate composition of glyphosate having an agronomically useful surfactant content, or that is "fully loaded" with surfactant, yet delivers to the weed control practitioner more glyphosate active ingredient per unit volume of concentrate than a comparably surfactant-containing or "fully loaded" composition based on glyphosate IPA salt.

An "agronomically useful surfactant content" means containing one or more surfactants of such a type or types and in such an amount that a benefit is realized by the user of the composition in terms of herbicidal effectiveness by comparison with an otherwise similar composition containing no surfactant. By "fully loaded" is meant having a sufficient concentration of a suitable surfactant to provide, upon conventional dilution in water and application to foliage, herbicidal effectiveness on one or more important weed species at least equal to that of current commercial glyphosate IPA salt products such as Roundup® herbicide, without the need for further surfactant to be added to the diluted composition.

By "storage-stable", in the context of an aqueous solution concentrate composition of glyphosate salt further containing a surfactant, is meant not exhibiting phase separation on exposure to temperatures up to about 50° C. (i.e., the composition must have a cloud point of about 50° C. or higher), and preferably not forming crystals of glyphosate or salt thereof on exposure to a temperature not lower than about 0° C. for a period of up to about 7 days. Ideally the cloud point should be 60° C. or higher, and the composition should withstand temperatures not lower than about –10° C. for up to about 7 days without crystal formation, even in the presence of seed crystals of the glyphosate salt.

A surfactant that is described herein as "compatible" with a glyphosate salt at specified surfactant and glyphosate a.e. concentrations is one that provides a storage-stable aqueous solution concentrate as defined immediately above containing that surfactant and salt at the specified concentrations.

Users of liquid herbicidal products typically meter the dosage by volume rather than by weight, and such products are usually labeled with directions for suitable use rates expressed in volume per unit area, e.g., liters per hectare (l/ha) or fluid ounces per acre (oz/acre). Thus the concentration of herbicidal active ingredient that matters to the user is not percent by weight, but weight per unit volume, e.g., grams per liter (g/l) or pounds per gallon (lb/gal). In the case of glyphosate salts, concentration is often expressed as grams of acid equivalent per liter (g a.e./l).

Historically, surfactant-containing glyphosate IPA salt products such as Roundup® and Roundup® Ultra herbicides of Monsanto Company have most commonly been formulated at a glyphosate concentration of about 360 g a.e./l. The surfactant-containing glyphosate TMS salt product Touchdown® of Zeneca has been formulated at a glyphosate concentration of about 330 g a.e./l. Products at lower a.e. concentration, i.e., more dilute, are also sold in some markets, but carry a cost penalty per unit of glyphosate they contain, primarily reflecting packaging, shipping and warehousing costs.

Further benefits in cost saving and in convenience to the user are possible if a "fully loaded" aqueous solution concentrate composition, or at least one having an agronomically useful surfactant content, can be provided at a glyphosate concentration significantly higher than 360 g a.e./l, for example about 420 g a.e./l or higher, or even about 480 g a.e./l or higher.

At very high glyphosate a.e. concentrations such as these, a significant problem normally occurs. This is the difficulty in pouring and/or pumping of the aqueous solution concentrate arising from the high viscosity of the concentrate, especially as manifested at low temperatures. It would therefore be highly desirable to have a highly concentrated aqueous solution of glyphosate salt that is less viscous than an aqueous solution of the IPA salt at the same glyphosate a.e. weight/volume concentration.

As will be clear from the disclosure that follows, these and other benefits are provided by the present invention.

SUMMARY OF THE INVENTION

Figure 1:
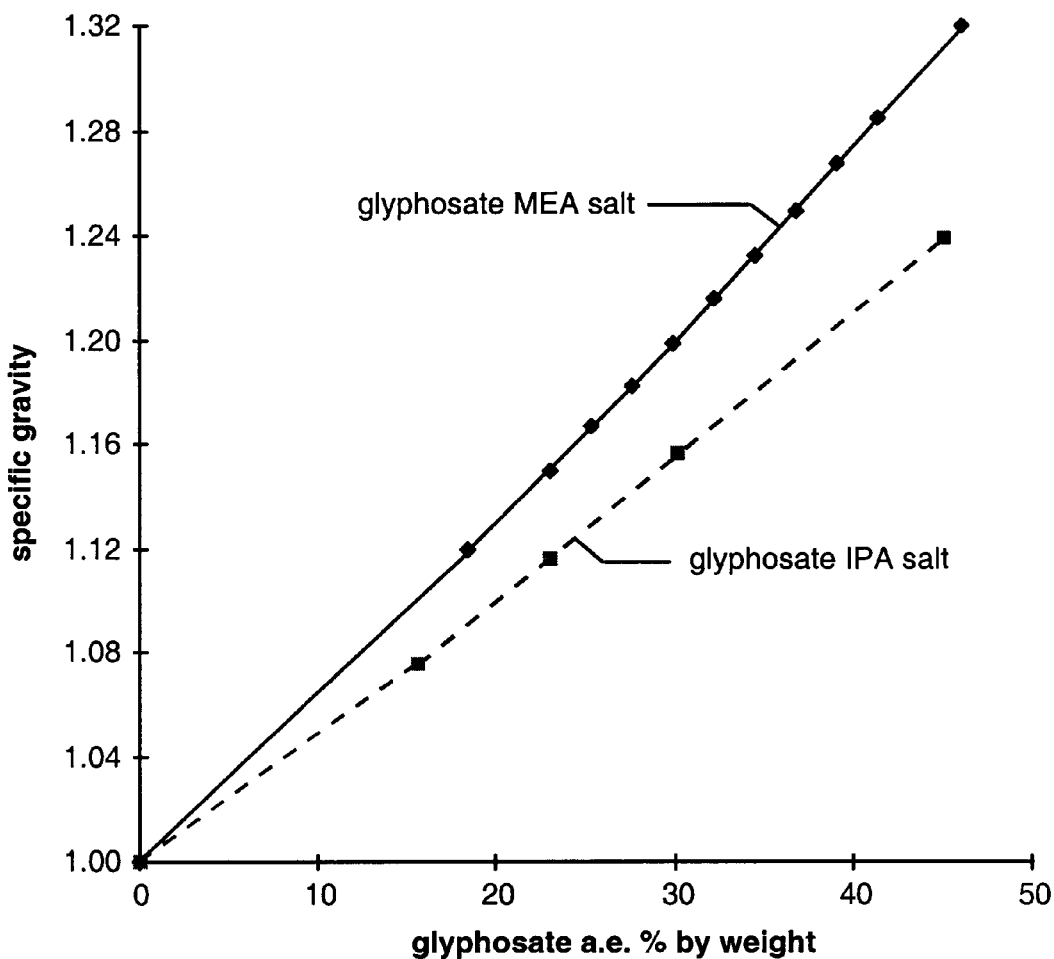
FIG. 1 is a graphical representation comparing, for glyphosate IPA and MEA salts, the relationship between weight percent concentration of glyphosate a.e. in an aqueous solution of the salt and the specific gravity of the aqueous solution.

The present invention takes advantage of a previously unknown and surprising property of concentrated aqueous solutions of glyphosate MEA salt, namely that such solutions have a very high specific gravity by comparison with aqueous solutions of most other organic ammonium salts of glyphosate, including the IPA salt, at the same glyphosate a.e. concentration. Accordingly, at a given percent concentration by weight, an aqueous solution concentrate composition of glyphosate MEA salt delivers to the user a significantly higher weight of active ingredient per unit volume of the composition than a corresponding composition of glyphosate IPA salt.

In one embodiment of the invention, therefore, there is provided a herbicidal composition comprising an aqueous solution of N-phosphonomethylglycine, predominantly in the form of the monoethanolammonium salt thereof, at a concentration of about 30 to about 48 percent, preferably about 40 to about 48 percent, N-phosphonomethylglycine acid equivalent by weight.

Such a composition, by virtue of its relatively high specific gravity, occupies a lesser volume than a corresponding composition of the isopropylammonium salt of N-phosphonomethylglycine at the same acid equivalent concentration by weight.

In a related embodiment of the invention, there is provided a herbicidal composition comprising an aqueous solution of N-phosphonomethylglycine, predominantly in the form of the monoethanolammonium salt thereof, at a concentration of about 360 to about 600 grams N-phosphonomethylglycine acid equivalent per liter of the composition.

Such a composition has a significantly lower viscosity than a corresponding composition of the isopropylammonium salt of N-phosphonomethylglycine at the same acid equivalent weight/volume concentration.

In a further embodiment of the invention, it has been found that in an aqueous solution concentrate formulation, an unexpectedly high weight/volume concentration of glyphosate MEA salt can be obtained in the presence of an agronomically useful surfactant content. The choice of surfactant has been found to be important to achieving this result.

In such embodiment, therefore, the present invention provides a herbicidal composition comprising:

(1) water;
(2) N-phosphonomethylglycine, predominantly in the form of the monoethanolammonium salt thereof, in solution in the water in an amount of about 360 to about 570 grams N-phosphonomethylglycine acid equivalent per liter of the composition; and
(3) a surfactant component in solution or stable dispersion in the water, comprising one or more surfactants in a total amount of about 20 to about 200 grams per liter of the composition, this surfactant component being selected such that the composition has a cloud point not lower than about 50° C. and preferably exhibits substantially no crystallization of glyphosate or salt thereof when stored at a temperature not lower than about 0° C. for a period of up to about 7 days.

The word "predominantly" in the above context means that at least about 50%, preferably at least about 75% and more preferably at least about 90%, by weight of the glyphosate, expressed as a.e., is present as the MEA salt. The balance can be made up of other salts and/or glyphosate acid so long as the cloud point and non-crystallization properties of the composition remain within the limits indicated.

As a further aspect of the present invention, a particular class of surfactants has been identified wherein compatibility with glyphosate MEA salt at the concentrations given above is unexpectedly high. Accordingly, an embodiment of the invention is a surfactant-containing herbicidal composition as described above wherein the surfactant component predominantly comprises one or more surfactants each having a molecular structure comprising:

(1) a hydrophobic moiety having one or a plurality of independently saturated or unsaturated, branched or unbranched, aliphatic, alicyclic or aromatic $C_{3-18}$ hydrocarbyl or hydrocarbylidene groups joined together by 0 to about 7 linkages independently selected from ether, thioether, sulfoxide, ester, thioester and amide linkages, this hydrophobic moiety having in total a number J of carbon atoms where J is about 8 to about 24; and
(2) a hydrophilic moiety comprising:
  (i) an amino group that is cationic or that can be protonated to become cationic, having attached directly thereto 0 to 3 oxyethylene groups or polyoxyethylene chains, these oxyethylene groups and polyoxyethylene chains comprising on average no more than a number E of oxyethylene units per surfactant molecule such that E+J=25; and/or
  (ii) a glycoside or polyglycoside group comprising on average no more than about 2 glycoside units per surfactant molecule.

In such surfactants the hydrophobic moiety is attached to the hydrophilic moiety in one of the following ways: (a) directly to an amino group if present, (b) by an ether linkage incorporating an oxygen atom of one of the oxyethylene groups if present or of a terminal oxyethylene unit of one of the polyoxyethylene chains if present, or (c) by an ether linkage to one of the glycoside units if present.

In the context of surfactant content, the expression "predominantly comprises" means that at least about 50%, preferably at least about 75% and more preferably at least about 90%, by weight of the surfactant component is made up of surfactants having the specified features of molecular structure. For the present purpose, the weight or concentration of surfactant component as defined herein does not include essentially non-surfactant compounds that are sometimes introduced with the surfactant component, such as water, isopropanol or other solvents, or glycols (such as ethylene glycol, propylene glycol, polyethylene glycol, etc.).

As further explanation of the relationship between E and J in polyoxyethylene amine surfactants, it has been found, surprisingly, that the larger the hydrophobic moiety (i.e., the higher the value of J) the fewer oxyethylene units can be present (i.e., the smaller is the value of E) for adequate compatibility with glyphosate MEA salt in a composition of the invention. For example, where J has an average value of about 18, as for example in a polyoxyethylene tallowamine, E, the maximum number of oxyethylene units, is about 7. However, where J has an average value of about 12, as in a polyoxyethylene cocoamine, E is about 13.

Without in any way limiting the scope of the present invention, two subclasses of surfactant, defined by formulas (V) and (VI) below, are particularly useful in compositions of the invention.

One embodiment of the invention is a herbicidal concentrate composition as described above wherein the surfactant component predominantly comprises one or more surfactants having, at a pH level of about 4, formula (V):

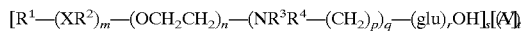

$[R^1—(XR^2)_m—(OCH_2CH_2)_n—(NR^3R^4—(CH_2)_p)_q—(glu)_rOH]_t[A]$ (V)

where $R^1$ is hydrogen or $C_{1-8}$ hydrocarbyl, each X is independently an ether, thioether, sulfoxide, ester, thioester or amide linkage, each $R^2$ is independently $C_{3-6}$ hydrocarbylidene, m is an average number of 0 to about 8, the total number of carbon atoms in $R^1—(XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a unit of formula

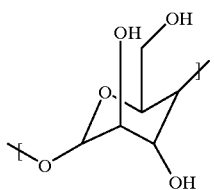

(referred to herein as a glucoside unit), r is an average number from 1 to about 2, A is an anionic entity, and s is an integer from 1 to 3 and t is 0 or 1 such that electrical neutrality is maintained.

Another embodiment of the invention is a herbicidal concentrate composition as described above wherein the surfactant component predominantly comprises one or more surfactants having, at a pH level of about 4, formula (VI):

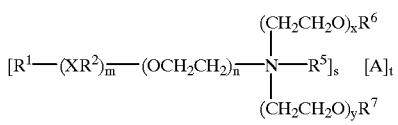

$$[R^1\!-\!(XR^2)_{\overline{m}}\!-\!(OCH_2CH_2)_{\overline{n}}\!-\!\overset{\overset{\displaystyle (CH_2CH_2O)_xR^6}{|}}{\underset{\underset{\displaystyle (CH_2CH_2O)_yR^7}{|}}{N}}\!-\!R^5]_s \quad [A]_t \qquad (VI)$$

where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 9, the total number J of carbon atoms in $R^1$—$(XR^2)_m$ is about 8 to about 24, n is an average number of 0 to about 5, $R^5$ is hydrogen, $C_{1-4}$ alkyl, benzyl, an anionic oxide group or an anionic group —$(CH_2)_uC(O)O$ where u is 1 to 3, $R^6$ and $R^7$ are independently hydrogen, $C_{1-4}$ alkyl or $C_{2-4}$ acyl, x and y are average numbers such that x+y+n is not greater than the number E as defined above, A is an anionic entity and s is an integer from 1 to 3 and t is 0 or 1 such that electrical neutrality is maintained.

It will be appreciated that surfactants conforming to formulas (V) or (VI) above include non-restrictively those that can be described as alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines, alkylamidopropylamines and the like, where the average number of oxyethylene units, if present, per surfactant molecule is no greater than 25-J where J is as defined above, and the average number of glucose units, if present, per surfactant molecule is no greater than about 2. The term "alkyl" as used in this paragraph reflects common usage in the art and means $C_{8-18}$ aliphatic, saturated or unsaturated, linear or branched hydrocarbyl.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Also provided by the present invention is a herbicidal method comprising diluting with a suitable volume of water a herbicidally effective volume of a composition as provided herein to form an application composition, and applying the application composition to foliage of a plant or plants.

DETAILED DESCRIPTION OF THE INVENTION

As indicated above, concentrated aqueous solutions of glyphosate MEA salt have surprisingly been found to have exceptionally high specific gravity. Table 2 shows, by way of example, specific gravities measured for 30% glyphosate a.e. by weight solutions of the MEA salt of glyphosate by comparison with other organic ammonium and other salts of current or previous commercial interest. Specific gravities are measured using a Mettler DA-300 Density/Specific Gravity Meter.

TABLE 2

Specific gravity (20/15.6° C.) of 30% a.e. by weight glyphosate monobasic salt solutions.

| Salt | Specific Gravity |
| --- | --- |
| monoethanolammonium (MEA) | 1.2357 |
| isopropylammonium (IPA) | 1.1554 |
| n-propylammonium | 1.1429 |
| methylammonium | 1.1667 |
| ethylammonium | 1.1599 |
| ammonium | 1.1814 |
| trimethylsulfonium (TMS) | 1.1904 |

Thus 1 liter of 30% a.e. by weight glyphosate MEA salt solution at 20° C. contains approximately 371 g glyphosate a.e./l, whereas 1 liter of 30% a.e. by weight glyphosate IPA salt solution at 20° C. contains approximately 347 g glyphosate a.e./l. In other words, at equal a.e. weight concentration, the MEA salt solution delivers about 7% more glyphosate a.e. per liter.

The higher specific gravity of solutions of the MEA salt becomes of particular value in surfactant-containing solutions, where the maximum glyphosate concentration is constrained not only by the limit of solubility of the MEA salt in water but also by the limits of surfactant compatibility. In such solutions, the advantages of the MEA salt can mean that (a) a higher maximum glyphosate a.e. weight/volume concentration is achieved than with the IPA salt in the presence of the same compatible surfactant at the same surfactant concentration, (b) a higher compatible surfactant concentration is achieved than with the IPA salt at the same glyphosate a.e. weight/volume concentration, (c) at given weight/volume concentrations of glyphosate a.e. and surfactant, improved storage-stability is achieved over a corresponding composition prepared with the IPA salt, and/or (d) at given weight/volume concentrations of glyphosate a.e. and surfactant, improved pouring and pumping properties are achieved over a corresponding composition prepared with the IPA salt as a result of lower viscosity.

The advantages of compositions of the present invention become less as glyphosate concentration is reduced and are only marginal at a glyphosate concentration lower than about 360 g a.e./l, i.e., lower than the concentration found in such commercial glyphosate IPA salt products as Roundup® herbicide. In preferred compositions of the invention, glyphosate concentration is not lower than 420 g a.e./l or about 420 g a.e./l, in particularly preferred compositions not lower than about 480 g a.e./l, for example about 480 to about 540 g a.e./l. It is believed that the upper limit of glyphosate concentration in a storage-stable surfactant-containing composition of the invention is about 570 g a.e./l, this limit being a consequence of the solubility limit of glyphosate MEA salt in water, compounded by further limitation due to the presence of surfactant.

Close to this upper limit of glyphosate concentration, the amount of surfactant that can be accommodated is less than at lower glyphosate concentrations. For most purposes, this small amount of surfactant is likely to be inadequate to give reliable enhancement of the herbicidal efficacy of the glyphosate to an acceptable degree. However, in certain special-purpose applications where the composition is to be diluted with a relatively small amount of water, for plant treatment at a volume of, for example, about 10 to about 50 l/ha, the surfactant concentration in a concentrate composition of the invention can usefully be as low as about 20 g/l. Such special-purpose applications include rope-wick application and ultra-low-volume aerial spraying. For general-purpose application, typically by spraying following dilution with about 50 to about 1000 l/ha, most commonly about 100 to about 400 l/ha, of water, the surfactant concentration in a concentrate composition of the invention is preferably about 60 to about 200 g/l.

Illustrative surfactant types that have been found useful in compositions of the invention include the following:

(A) Surfactants corresponding to formula (V) where $R^1$ is a $C_{8-18}$ aliphatic, saturated or unsaturated, linear or branched hydrocarbyl chain, m, n and q are 0, s is 1 and t is 0. This group includes several commercial surfactants collectively known in the art or referred to herein as "alkyl polyglucosides" or "APGs". Suitable examples are sold by Henkel as Agrimul™ PG-2069 and Agrimul™ PG-2076.

(B) Surfactants corresponding to formula (VI) where $R^1$ is a $C_{8-18}$ aliphatic, saturated or unsaturated, linear or branched hydrocarbyl chain and m is 0. In this group $R^1$ alone forms the hydrophobic moiety of the surfactant and is attached directly to the amino function, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include:

(B-1) Surfactants wherein x and y are 0, $R^5$ and $R^6$ are independently $C_{1-4}$ alkyl, $R^7$ is hydrogen and t is 1. This subtype includes (where $R^5$ and $R^6$ are each methyl) several commercial surfactants known in the art or referred to herein as "alkyldimethylamines". Suitable examples are dodecyldimethylamine, available for example from Akzo as Armeen™ DM12D, and cocodimethylamine and tallowdimethylamine, available for example from Ceca as Noram™ DMC D and Noram™ DMS D respectively. Such surfactants are generally provided in non-protonated form, the anion A not being supplied with the surfactant. However, in a glyphosate MEA salt formulation at a pH of about 4–5, the surfactant will be protonated and it will be recognized that the anion A can be glyphosate, which is capable of forming dibasic salts.

(B-2) Surfactants wherein x and y are 0, $R^5$, $R^6$ and $R^7$ are independently $C_{1-4}$ alkyl and t is 1. This subtype includes (where $R^5$, $R^6$ and $R^7$ are each methyl and A is a chloride ion) several commercial surfactants known in the art or referred to herein as "alkyltrimethylammonium chlorides". A suitable example is cocoalkyl trimethylammonium chloride, available for example from Akzo as Arquad™ C.

(B-3) Surfactants wherein x+y is 2 or greater, $R^6$ and $R^7$ are hydrogen and t is 1. This subtype includes commercial surfactants known in the art or referred to herein as "polyoxyethylene alkylamines" (where n is 0 and $R^5$ is hydrogen), certain "polyoxyethylene alkyletheramines" (where n is 1–5 and $R^5$ is hydrogen), "polyoxyethylene N-methyl alkylammonium chlorides" (where n is 0 and $R^5$ is methyl), and certain "polyoxyethylene N-methyl alkyletherammonium chlorides" (where n is 1–5 and $R^5$ is methyl). Suitable examples are polyoxyethylene (2) cocoamine, polyoxyethylene (5) tallowamine and polyoxyethylene (10) cocoamine, available for example from Akzo as Ethomeen™ C/12, Ethomeen™ T/15 and Ethomeen™ C/20 respectively; a surfactant conforming, when its amine group is non-protonated, to formula (VII):

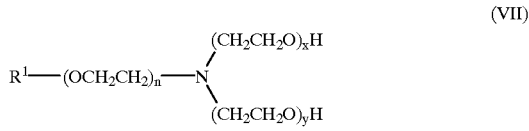

where $R^1$ is $C_{12-15}$ alkyl and x+y is 5, as disclosed in U.S. Pat. No. 5,750,468; and polyoxyethylene (2) N-methyl cocoammonium chloride and polyoxyethylene (2) N-methyl stearylammonium chloride, available for example from Akzo as Ethoquad™ C/12 and Ethoquad™ 18/12 respectively. In cases where $R^5$ is hydrogen, i.e., in tertiary as opposed to quaternary ammonium surfactants, the anion A is typically not supplied with the surfactant. However, in a glyphosate MEA salt formulation at a pH of about 4–5, it will be recognized that the anion A can be glyphosate, which is capable of forming dibasic salts.

(B-4) Surfactants wherein $R^5$ is an anionic oxide group and t is 0. This subtype includes commercial surfactants known in the art or referred to herein as "alkyldimethylamine oxides" (where n, x and y are 0, and $R^6$ and $R^7$ are methyl), certain "alkyletherdimethylamine oxides" (where n is 1–5, x and y are 0, and $R^6$ and $R^7$ are methyl), "polyoxyethylene alkylamine oxides" (where n is 0, x+y is 2 or greater, and $R^6$ and $R^7$ are hydrogen), and certain "polyoxyethylene alkyletheramine oxides" (where n is 1–5, x+y is 2 or greater, and and $R^6$ and $R^7$ are hydrogen). Suitable examples are cocodimethylamine oxide, sold by Akzo as Aromox™ DMC, and polyoxyethylene (2) cocoamine oxide, sold by Akzo as Aromox™ C/12.

(B-5) Surfactants wherein $R^5$ is an anionic group —$CH_2C(O)O$(acetate), x and y are 0 and t is 0. This subtype includes commercial surfactants known in the art or referred to herein as "alkylbetaines" (where n is 0, $R^5$ is acetate and $R^6$ and $R^7$ are methyl) and certain "alkyletherbetaines" (where n is 1–5, $R^5$ is acetate and $R^6$ and $R^7$ are methyl). A suitable example is cocobetaine, sold for example by Henkel as Velvetex™ AB-45.

(C) Surfactants corresponding to formula (VI) where $R^1$ is a $C_{8-18}$ aliphatic, saturated or unsaturated, linear or branched hydrocarbyl chain, m is 1, X is an ether linkage, $R^2$ is n-propylene and n is 0. In this group $R^1$ together with $OR^2$ forms the hydrophobic moiety of the surfactant which is attached directly by the $R^2$ linkage to the amino function. These surfactants are a subclass of alkyletheramines as disclosed in U.S. Pat. No. 5,750,468. Illustrative subtypes have the different hydrophilic moieties exemplified in (B-1) to (B-5) above. Suitable examples are a surfactant conforming, when its amine group is non-protonated, to formula (VIII):

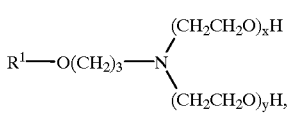

(VIII)

a surfactant conforming to formula (IX):

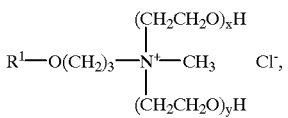

(IX)

and a surfactant conforming to formula (X):

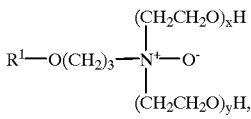

(X)

where, in each of formulas (VIII), (IX) and (X), $R^1$ is $C_{12-15}$ alkyl and x+y is 5, as disclosed in U.S. Pat. No. 5,750,468.

(D) Surfactants corresponding to formula (VI) where $R^1$ is a $C_{8-18}$ aliphatic, saturated or unsaturated, linear or branched hydrocarbyl chain, m is 1–5, each $XR^2$ is a group —OCH(CH$_3$)CH$_2$— and n is 0. In this group $R^1$ together with the —OCH(CH$_3$)CH$_2$— groups forms the hydrophobic moiety of the surfactant which is attached directly to the amino function. These surfactants are a further subclass of alkyletheramines as disclosed in U.S. Pat. No. 5,750,468. Illustrative subtypes have the different hydrophilic moieties exemplified in (B-1) to (B-5) above. A suitable example is a surfactant conforming, when its amine group is non-protonated, to formula (XI):

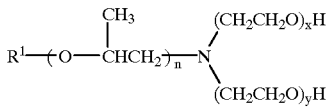

(XI)

where $R^1$ is $C_{12-15}$ alkyl, m is 2 and x+y is 5 as disclosed in U.S. Pat. No. 5,750,468.

(E) Surfactants corresponding to formula (VI) where $R^1$ is a $C_{8-18}$ aliphatic, saturated or unsaturated, linear or branched hydrocarbyl chain, m is 1, X is an amide linkage, $R^2$ is n-propylene and n is 0. In this group $R^1$ together with $XR^2$ forms the hydrophobic moiety of the surfactant which is attached directly by the $R^2$ linkage to the amino function. In preferred surfactants of this group, x and y are 0, $R^5$ is hydrogen or $C_{1-4}$ alkyl, $R^6$ and $R^7$ are independently $C_{1-4}$ alkyl and t is 1. A suitable example is cocoamidopropyl dimethylamine propionate, sold for example by McIntyre as Mackalene™ 117.

(F) Surfactants corresponding to formula (VI) where $R^1$ is hydrogen, m is 3–8 and each $XR^2$ is a group —OCH (CH$_3$)CH$_2$—. In this group the polyether chain of —OCH(CH$_3$)CH$_2$— groups (a polyoxypropylene chain) forms the hydrophobic moiety of the surfactant which is linked directly or via one or more oxyethylene units to the amino function. In preferred surfactants of this group, x and y are 0, $R^5$, $R^6$ and $R^7$ are independently $C_{1-4}$ alkyl and t is 1. These surfactants are a subclass of the polyoxypropylene quaternary ammonium surfactants disclosed in U.S. Pat. No. 5,652,197. In a suitable example, m is 7, n is 1, $R^5$, $R^6$ and $R^7$ are each methyl, and A is chloride.

In surfactants where t is 1, A can be any suitable anion but preferably is chloride, bromide, iodide, sulfate, ethosulfate, phosphate, acetate, propionate, succinate, lactate, citrate or tartrate, or, as indicated above, glyphosate.

In one embodiment of the invention the composition contains a surfactant of a class of alkyletheramines disclosed in U.S. Pat. No. 5,750,468. In a further embodiment, surfactants present are other than alkyletheramines as disclosed in U.S. Pat. No. 5,750,468.

A particular embodiment of the invention is a glyphosate MEA salt composition as described above wherein the glyphosate concentration, expressed in g a.e./l, is higher than the maximum concentration that would provide acceptable storage-stability if all the glyphosate were instead present as the IPA salt. Again, by acceptable storage-stability is meant having a cloud point not lower than about 50° C., and preferably exhibiting substantially no formation of crystals of glyphosate or salt thereof when exposed to temperatures not lower than about 0° C. for a period of up to about 7 days.

Another particular embodiment of the invention is a glyphosate MEA salt composition as described above having lower viscosity than an otherwise similar composition wherein all the glyphosate is instead in the form of the IPA salt. It is particularly useful if the lower viscosity is manifested as improved pourability and/or pumpability at low temperatures, for example about –10° C. to about 10° C. It has been discovered, surprisingly, that reduced viscosity is a feature of virtually all aqueous concentrate compositions of glyphosate MEA salt, when compared with corresponding compositions of glyphosate IPA salt. This discovery is especially well illustrated by Example 4 herein, and in particular by the data in Table 6 forming part of that Example.

Where, in an aqueous concentrate composition, the concentration of glyphosate salt and/or the concentration of surfactant are so high that viscosity is unacceptably high even with the MEA salt, the MEA salt nonetheless provides a significant advantage over the IPA salt. In such a composition, addition of a small amount of water typically lowers the viscosity to a much greater degree when the glyphosate is present as the MEA salt rather than the IPA salt. The amount of water required to lower viscosity to any desired level is significantly less in the case of the MEA salt than in the case of the IPA salt.

It has unexpectedly been found that replacement of glyphosate IPA salt by glyphosate MEA salt in a surfactant-containing aqueous solution concentrate composition can provide a further benefit in the form of reduced irritancy to eyes. This is especially surprising as it is known that it is the surfactant component of such compositions, especially where the predominant surfactant is an amine-based surfactant, that is primarily responsible for any eye irritancy exhibited. Accordingly, a further particular embodiment of the invention is a glyphosate MEA salt composition as described above having lower eye irritancy than an otherwise similar composition wherein all the glyphosate is instead in the form of the IPA salt.

Although the present invention is directed primarily at aqueous solution concentrate formulations of the MEA salt of glyphosate, such aqueous solution concentrate formulations can optionally further comprise one or more additional water-soluble herbicidal active ingredients, including without restriction water-soluble forms of acifluorfen, asulam, benazolin, bentazon, bialaphos, bispyribac, bromacil, bromoxynil, carfentrazone, chloramben, clopyralid, 2,4-D, 2,4-DB, dalapon, dicamba, dichlorprop, diclofop, difenzoquat, diquat, endothall, fenac, fenoxaprop, flamprop, fluazifop, fluoroglycofen, fluroxypyr, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA and triclopyr. Where the additional herbicide is anionic, like glyphosate, it is preferred that the additional herbicide is likewise present predominantly as the MEA salt.

An embodiment of the invention therefore is an herbicidal aqueous solution concentrate composition comprising glyphosate predominantly in the form of the MEA salt thereof, and a second anionic herbicide predominantly in the form of the MEA salt thereof, the total concentration of the glyphosate and the second anionic herbicide together being about 360 to about 570 g a.e./l, the composition further comprising a surfactant component, selected in accordance with the invention, at a concentration of about 20 to about 200 g/l.

In this embodiment, it is preferred that the weight/weight ratio of glyphosate a.e. to the second anionic herbicide be not less than about 1:1, for example from about 1:1 to about 30:1. The second anionic herbicide is preferably selected from the group consisting of acifluorfen, bialaphos, carfentrazone, clopyralid, 2,4-D, 2,4-DB, dicamba, dichlorprop, glufosinate, MCPA, MCPB, mecoprop, methylarsonic acid, nonanoic acid, picloram, triclopyr and herbicides of the imidazolinone class, including imazameth, imazamethabenz, imazamox, imazapic, imazapyr, imazaquin and imazethapyr.

Also embraced by the present invention are liquid concentrate formulations having an aqueous phase wherein glyphosate is present predominantly in the form of the MEA salt thereof, and a non-aqueous phase optionally containing a second herbicidal active ingredient that is relatively water-insoluble. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations of the invention having a non-aqueous phase, the concentration of glyphosate a.e. in the composition as a whole is nonetheless within the ranges recited herein for aqueous solution concentrate formulations.

Illustrative water-insoluble herbicides that can be used in such formulations include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flurniclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamnide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate. It is preferred that the weight/weight ratio of glyphosate a.e. to such water-insoluble herbicide be not less than 1:1, for example from about 1:1 to about 30:1.

Excipient ingredients other than the above-defined surfactant component can optionally be present in a composition of the invention, so long as the cloud point and non-crystallization properties of the composition remain in accordance with the invention. Such additional excipient ingredients include conventional formulation additives such as dyes, thickeners, crystallization inhibitors, antifreeze agents including glycols, foam moderating agents, antidrift agents, compatibilizing agents, etc.

A type of excipient ingredient often used in glyphosate formulations is an inorganic salt such as ammonium sulfate, included to enhance herbicidal activity, or consistency of herbicidal activity, of the glyphosate. As the content of inorganic salt in the formulation needed to provide such enhancement is typically relatively high, often greater than the amount of glyphosate present, it will seldom be useful to add such salt to a composition of the invention. The amount of ammonium sulfate, for example, that could be accommodated in a storage-stable aqueous composition containing glyphosate MEA salt at a concentration of at least 360 g a.e./l would be so small as to bring no substantial benefit. An alternative, therefore, is to include a small amount of a synergist such as an anthraquinone compound or a phenyl-substituted olefin compound as disclosed in International Publication Nos. WO 98/33384 and WO 98/33385 respectively.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate salts are used to control a very wide variety of plants worldwide, and it is believed the MEA salt will prove no different from other salts of glyphosate in this regard.

Particularly important annual dicotyledonous plant species for control of which a composition of the invention can be used are exemplified without limitation by velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.).

Particularly important annual monocotyledonous plant species for control of which a composition of the invention can be used are exemplified without limitation by wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial dicotyledonous plant species for control of which a composition of the invention can be used are exemplified without limitation by mugwort (Artemisia spp.), milkweed (Asclepias spp.), canada thistle (*Cirsium arvense*), field bindweed (*Convolvulus arvensis*) and kudzu (Pueraria spp.).

Particularly important perennial monocotyledonous plant species for control of which a composition of the invention can be used are exemplified without limitation by brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial plant species for control of which a composition of the invention can be used are exemplified without limitation by horsetail (Equisetum spp.), bracken (*Pteridium aquilinum*), blackberry (Rubus spp.) and gorse (*Ulex europaeus*).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

In a particular contemplated method of use of a composition of the invention, the composition, following dilution in water, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include, without restriction, varieties of cotton, soybean, canola, sugar beet and corn.

Plant treatment compositions can be prepared simply by diluting a concentrate composition of the invention in water. Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Useful spray volumes for the present invention can range from about 10 to about 1000 liters per hectare (l/ha) or higher, by spray application.

EXAMPLES

The following Examples are provided for illustrative purposes only and are not intended to limit the scope of the present invention. The Examples will permit better understanding of the invention and perception of its advantages and certain variations of execution.

Example 1

In a 1 liter glass vessel with magnetic stirrer are mixed 479.2 g glyphosate acid, technical grade (assay 96%), 166.0 g monoethanolamine and water to 1000 g. Reaction of the glyphosate acid with the monoethanolamine to form the MEA salt of glyphosate is exothermic. The reaction mixture is allowed to cool to room temperature. The specific gravity (20/15.6° C.) of the resulting 62.6% by weight aqueous solution of glyphosate MEA salt, containing 46.0% by weight glyphosate a.e., is measured and found to be 1.32. The density of the solution at 25° C. is 1.31 g/l, thus the volume at 25° C. of 1000 g of this solution is 763 ml and the weight/volume concentration of glyphosate is 602 g a.e./l.

For comparison, a 62.1% by weight aqueous solution of glyphosate IPA salt, also containing 46.0% by weight glyphosate a.e., is found to have a specific gravity of 1.24. The density of the solution at 25° C. is 1.23 g/l, thus the volume at 25° C. of 1000 g of this comparative solution is 813 ml and the weight/volume concentration of glyphosate is 565 g a.e./l.

Example 2

A series of aqueous solutions of glyphosate MEA salt, having a range of glyphosate a.e. concentrations, are prepared by the general procedure of Example 1. Specific gravity is measured for each solution.

Results are shown in FIG. 1, by comparison with solutions of glyphosate IPA salt. At all concentrations, specific gravity of the MEA salt solution is found to be significantly higher than that of the corresponding IPA salt solution.

Example 3

A 46% a.e. by weight aqueous solution of glyphosate MEA salt is prepared as described in Example 1. A comparative 46% a.e. by weight aqueous solution of glyphosate IPA salt is also prepared.

Viscosity of each solution is measured at 25° C. using a Brookfield viscometer set at 6 rpm using spindle #18. The IPA salt solution is found to have a viscosity of 165 cPs, whereas the MEA salt surprisingly has a viscosity of only 88 cPs.

Example 4

Surfactant-containing compositions 4-01 to 4-11 are prepared as described below. Each contains glyphosate MEA salt, and is prepared using a 46% a.e. by weight, 602 g a.e./l aqueous solution thereof prepared as in Example 1. The surfactant in each case is selected from the list provided in Table 3 below. Comparative compositions are prepared with glyphosate IPA salt, which is added as a 46% a.e. by weight, 565 g a.e./l aqueous solution thereof as described in Example 1.

TABLE 3

Surfactants used in compositions of Example 4.

| Surfactant | Chemical description | Trade name and supplier |
|---|---|---|
| A | polyoxyethylene (5) cocoamine | Ethomeen ™ C/15 (Akzo) |
| B | N-cocoalkyl-N-methyl-N,N-diethanolammonium chloride | Ethoquad C/12-W (Akzo) |
| C | N-cocoalkyl-N,N-diethanolamine oxide | Aromox ™ C/12 (Akzo) |
| D | compound of formula (VIII) where $R^1$ is isotridecyl and $x + y = 5$ | E-17-5 (Tomah) |
| E | compound of formula (IX) where $R^1$ is isodecyl and $x + y = 2$ | Q-14-2 (Tomah) |
| F | compound of formula (XI) where $R^1$ is $C_{12-14}$ alkyl, $n = 2$ and $x + y = 5$ | not commercially available* |

*A method of making this surfactant is disclosed in United Kingdom Patent No. 1,588,079

Target weight/volume concentrations, expressed below in the format [glyphosate a.e.]/[surfactant], the units being g/l, are established. Actual weight/volume concentrations can differ slightly from target concentrations because the ingredients are measured by weight for convenience. Amounts of ingredients mixed to provide the various target concentrations are as shown in Table 4 (for glyphosate MEA salt compositions of the invention) and Table 5 (for comparative glyphosate IPA salt compositions).

TABLE 4

Amounts of ingredients used in preparing glyphosate MEA salt compositions of Example 4.

| Target weight/volume concentrations (g/l) | 46% MEA salt solution (g) | Surfactant (g) | Water (g) |
|---|---|---|---|
| 490/100 | 82.94 | 8.00 | 9.06 |
| 480/120 | 81.24 | 10.00 | 8.76 |
| 480/80 | 81.45 | 6.40 | 12.15 |
| 480/60 | 81.45 | 4.80 | 13.75 |
| 445/110 | 76.46 | 8.86 | 14.68 |

TABLE 5

Amounts of ingredients used in preparing comparative glyphosate IPA salt compositions of Example 4.

| Target weight/volume concentrations (g/l) | 46% IPA salt solution (g) | Surfactant (g) | Water (g) |
|---|---|---|---|
| 490/100 | 90.01 | 8.30 | 0.79 |
| 480/120 | 88.69 | 10.00 | 1.31 |
| 480/80 | 88.69 | 6.70 | 4.61 |
| 480/60 | 88.69 | 5.00 | 6.31 |
| 445/110 | 81.00 | 9.20 | 9.80 |

Specific gravity (20/15.6° C.), viscosity at 25° C. and cloud point are recorded for each composition prepared as shown in Table 6.

TABLE 6

Data on compositions of Example 4.

| Composition no. | Target concentrations | Surfactant | Glyphosate salt | Specific gravity | Viscosity at 25° C. (cPs) | Cloud point (° C.) |
|---|---|---|---|---|---|---|
| 4-01 | 480/120 | A | MEA | 1.2561 | 73 | >95 |
|  |  |  | IPA | 1.2100 | 474 | >95 |
| 4-02 | 480/120 | B | MEA | 1.2601 | 35 | >95 |
|  |  |  | IPA | 1.2096 | 126 | >95 |
| 4-03 | 480/120 | C | MEA | 1.2509 | 128 | 55 |
|  |  |  | IPA | 1.1989 | 259 | >95 |
| 4-04 | 480/120 | D | MEA | 1.2613 | 329 | 82 |
|  |  |  | IPA | 1.2098 | 461 | 88 |
| 4-05 | 445/110 | D | MEA | 1.2349 | 70 | 73 |
|  |  |  | IPA | 1.1899 | 210 | 92 |
| 4-06 | 480/120 | E | MEA | 1.2479 | 217 | >95 |
|  |  |  | IPA | 1.2041 | 448 | >95 |
| 4-07 | 490/100 | F | MEA | 1.2655 | 83 | 71 |
|  |  |  | IPA | 1.2152 | 349 | 78 |
| 4-08 | 480/120 | F | MEA | 1.2593 | 93 | 70 |
|  |  |  | IPA | 1.2078 | 382 | 79 |
| 4-09 | 480/80 | F | MEA | 1.2574 | 54 | 71 |
|  |  |  | IPA | 1.2105 | 185 | 76 |
| 4-10 | 480/60 | F | MEA | 1.2613 | 45 | 70 |
|  |  |  | IPA | 1.2098 | 132 | 85 |
| 4-11 | 445/110 | F | MEA | 1.2438 | 49 | >95 |
|  |  |  | IPA | 1.1939 | 157 | 81 |

It will be noted in Table 6 that all compositions of the invention containing glyphosate MEA salt have significantly lower viscosity than corresponding IPA salt compositions. The magnitude of this viscosity advantage in favor of the MEA salt compositions depends to some extent on the choice and concentration of surfactant. For example, composition 4-01 of the invention, having target concentrations of 480 g/l glyphosate a.e. in the form of MEA salt and 120 g/l polyoxyethylene (5) cocoamine surfactant, exhibits an especially great advantage over the comparative IPA salt composition.

In some but not all cases illustrated in Table 6, a glyphosate MEA salt composition exhibits a lower cloud point than the corresponding IPA salt composition. However, in none of these cases is the cloud point lower than 50° C., and in only one case (composition 4-03) does cloud point approach this lower limit of commercial acceptability. Thus, in general, where a reduction in cloud point occurs with replacement of IPA salt by MEA salt, this reduction is an acceptable trade-off for the major advantage in viscosity, and thus in pouring and pumping behavior, enabled by such replacement.

Example 5

The maximum surfactant concentration attainable in practice in an aqueous concentrate composition containing glyphosate salt at 540 g a.e./l is compared for MEA and IPA salts. This is determined by adding a selected surfactant in increments to a 46% a.e. by weight aqueous solution of the glyphosate salt until the glyphosate weight/volume concentration falls from its initial level (565 g a.e./l for IPA salt, 602 g a.e./l for MEA salt) to 540 g a.e./l. The study is conducted using either Surfactant A or Surfactant F of Table 3 above. When the maximum attainable surfactant concentration is reached, viscosity is measured at 25° C. Results are shown in Table 7. Note that a composition having the maximum attainable surfactant concentration as determined by this procedure does not necessarily exhibit acceptable stability as measured by cloud point and/or crystal formation.

TABLE 7

Maximum attainable surfactant concentration in an aqueous concentrate composition having 540 g/l glyphosate a.e. concentration.

| Glyphosate salt | Surfactant | Maximum attainable surfactant concentration (g/l) | Viscosity at 25° C. (cPs) |
|---|---|---|---|
| MEA | A | 116 | 210 |
| IPA | A | 46 | 384 |
| MEA | F | 119 | 210 |
| IPA | F | 46 | 362 |

The data in Table 7 illustrate one of the most beneficial advantages of glyphosate MEA salt compositions, and one of the most surprising, particularly in view of the relative incompatibility of the MEA salt with polyoxyethylene (15) tallowamine, the hitherto most widely used surfactant in glyphosate IPA salt compositions, as indicated in Table 1. As shown in Table 7, it is possible, using the MEA salt, to achieve, at the extremely high glyphosate a.e. concentration of 540 g a.e./l, a concentration of selected surfactant more than 2.5 times the maximum attainable using the IPA salt. Furthermore, with the MEA salt the surfactant/glyphosate a.e. weight ratio is greater than 1:5, a level consistent with commercially acceptable herbicidal efficacy, whereas with the IPA salt this ratio is well below 1:10. Equally importantly, the surfactants illustrated in Table 7 are known in the art to be highly effective in enhancing glyphosate herbicidal efficacy at surfactant/glyphosate a.e. ratios of 1:5 or greater (see, for example, U.S. Pat. No. 5,668,085 with regard to Surfactant A and U.S. Pat. No. 5,750,468 with regard to Surfactant F). Thus a composition that can take advantage of such surfactants, yet provide a glyphosate a.e. loading as high as 540 g a.e./l, is a significant advance in the art that could not have been predicted from prior knowledge of these surfactants or of glyphosate MEA salt.

Even more surprising is the finding, as shown in Table 7, that even with the much higher surfactant concentration attainable with the MEA salt, viscosity of the MEA salt compositions is nonetheless much lower than that of the IPA salt compositions. The IPA salt compositions have not only a low surfactant concentration unlikely to provide commercially acceptable herbicidal efficacy, especially at higher spray volumes, but also a high viscosity unlikely to permit commercially acceptable pouring or pumping behavior, especially at lower temperatures than exemplified in Table 7. By contrast, the MEA salt compositions not only can be expected to deliver good herbicidal efficacy, but also do not present a pouring or pumping problem.

Theoretically it is possible to attain slightly higher surfactant concentrations than shown in this Example by starting with a glyphosate MEA or IPA salt solution even more concentrated than 46% a.e. by weight. However, the glyphosate salt concentration of the resulting composition will then be so close to the limit of solubility that in practice the composition is unlikely to have acceptable storage-stability, and in particular is likely to exhibit deposition of crystals of glyphosate or salt thereof, particularly at low temperatures.

Example 6

Storage-stability at low temperature is compared for four compositions. Composition 6-01 contains glyphosate MEA salt at a concentration of 540 g a.e./l and surfactant A at 46 g/l. Composition 6-02 is similar but with surfactant F at 46 g/l. Comparative compositions are prepared in each case, using glyphosate IPA salt in place of glyphosate MEA salt, but with the same surfactants at the same concentration of 46 g/l, the maximum attainable with the IPA salt as shown in Example 5.

Compositions are placed in capped glass bottles in a refrigerated storage area at 0° C. for 3 days. A seed crystal of the same glyphosate salt as used in preparing the composition is then added, and the compositions are stored for a further 7 days. At the end of this period, the compositions are examined for crystal growth.

No crystal growth is evident for the MEA salt compositions 6-01 and 6-02, but significant crystal growth is seen in both comparative IPA salt compositions. This illustrates a further advantage of compositions of the invention at high glyphosate concentration, namely improved low temperature storage-stability.

Example 7

Glyphosate MEA salt compositions 7-01 and 7-02 are prepared, substantially identical to compositions 4-08 and 4-11 respectively, and comparative IPA salt compositions are likewise prepared. Viscosity is measured at 25° C. and at a series of lower temperatures, to verify that the low viscosity advantage seen at 25° C. for MEA salt compositions continues to hold true at the lower temperatures, where in practice most pouring and pumping problems are seen. Results are shown in Table 8.

TABLE 8

Low temperature viscosity of compositions of Example 7.

| Composition no. | Target concentrations | Surfactant | Glyphosate salt | Viscosity (cPs), at ° C. | | | | |
|---|---|---|---|---|---|---|---|---|
| | | | | 25 | 20 | 15 | 10 | 0 |
| 7-01 | 480/120 | F | MEA | 110 | 118 | 170 | 229 | 456 |
| | | | IPA | 262 | 426 | 541 | 889 | 2300 |
| 7-02 | 445/110 | F | MEA | 45 | n.d. | 69 | 104 | 180 |
| | | | IPA | 122 | n.d. | 198 | 296 | 654 | n d. = not determined

As shown in Table 8, the low viscosity advantage of glyphosate MEA salt compositions of the invention over the corresponding IPA salt compositions becomes even more significant at lower temperatures.

Example 8

Glyphosate MEA salt composition 8-01 is prepared, substantially identical to compositions 4-08 and 7-01, having a glyphosate concentration of 480 g a.e./l, and a glyphosate IPA salt composition having the same glyphosate concentration and the same surfactant F at the same 120 g/l concentration is prepared for comparative purposes.

A standard eye irritation test is conducted on these compositions, following U.S. Environmental Protection Agency (EPA) assessment guidelines, subsection F, *Hazard Evaluation: Human and Domestic Animals* (Revised edition, 1984), Section 81-4, *Primary Eye Irritation*. The comparative IPA salt composition is found to cause eye irritation sufficient to place that composition in the most severely irritant class (Category I) used by EPA in classifying pesticide formulations. By comparison, composition 8-01 of the invention is found to cause a lesser degree of eye irritation, placing that composition in Category II.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A herbicidal concentrate composition comprising
   (1) water;
   (2) N-phosphonomethylglycine, predominantly in the form of the monoethanolammonium salt thereof, in solution in said water in an amount of about 360 to about 570 grams acid equivalent per liter of the composition; and
   (3) a surfactant component in solution or stable dispersion in said water, comprising one or more surfactants in a total amount of about 20 to about 200 grams per liter of the composition;
   wherein said surfactant component is selected such that the composition has a cloud point not lower than about 50° C. and said surfactant component predominantly comprises one or more surfactants each having a molecular structure comprising
   (1) a hydrophobic moiety having one or a plurality of independently saturated or unsaturated, branched or unbranched, aliphatic, alicyclic or aromatic $C_{3-8}$ hydrocarbyl or hydrocarbylidene groups joined together by 0 to about 7 linkages selected from ether, thioether, sulfoxide, ester, thioester and amide linkages, said hydrophobic moiety having in total a number J of about 8 to about 24 carbon atoms, and
   (2) a hydrophilic moiety comprising
      (i) an amino group that is cationic or that can be protonated to become cationic, having attached directly thereto 0 to 3 oxyethylene groups or polyoxyethylene chains, said oxyethylene groups and polyoxyethylene chains comprising on average no more than a number E of oxyethylene units per surfactant molecule such that E+J=25, and/or
      (ii) a glycoside or polyglycoside group comprising on average no more than about 2 glycoside units per surfactant molecule,
   said hydrophobic moiety being attached (a) directly to an amino group of said hydrophilic moiety, (b) to said hydrophilic moiety by an ether linkage incorporating an oxygen atom of one of said oxyethylene groups or of a terminal oxyethylene unit of one of said polyoxyethylene chains, or (c) to said hydrophilic moiety by an ether linkage to one of said glycoside units.

2. A herbicidal concentrate composition comprising
   (1) water;
   (2) N-phosphonomethvlglycine, predominantly in the form of the monoethanolammonium salt thereof, in solution in said water in an amount of about 360 to about 570 grams acid equivalent per liter of the composition; and
   (3) a surfactant component in solution or stable dispersion in said water comprising one or more surfactants in a total amount of about 20 to about 200 grams per liter of the composition;
   wherein said surfactant component is selected such that the composition has a cloud point not lower than about 50° C. and said surfactant component predominantly comprises one or more compounds having, at a pH level of about 4, the formula $$[R^1-(XR^2)_m-(OCH_2CH_2)_n-(NR^3R^4-(CH_2)_p)_q-(glu)_r-OH]_s[A]_t$$

where $R^1$ is hydrogen or $C_{1-18}$ hydrocarbyl, each X is an ether, thioether, sulfoxide, ester, thioester or amide linkage, each $R^2$ is independently $C_{3-6}$ hydrocarbylidene, m is an average number of 0 to about 8, the total number of carbon atoms in $R^1-(XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a glucoside unit, r is an average number from 1 to about 2, A is an anionic entity, and s is an integer from 1 to 3 and t is 0 or 1 such that electrical neutrality is maintained.

3. The composition of claim 2 wherein $R^1$ is a $C_{8-18}$ aliphatic, saturated or unsaturated, linear or branched hydrocarbyl chain, m, n and q are 0, s is 1 and t is 0.

4. A herbicidal concentrate composition comprising
(1) water;
(2) N-phosphonomethylglycine, predominantly in the form of the monoethanolammonium salt thereof, in solution in said water in an amount of about 360 to about 570 grams acid equivalent per liter of the composition; and
(3) a surfactant component in solution or stable dispersion in said water, comprising one or more surfactants in a total amount of about 20 to about 200 grams per liter of the composition;
wherein said surfactant component is selected such that the composition has a cloud point not lower than about 50° C. and said surfactant component predominantly comprises one or more compounds having, at a pH level of about 4, the formula

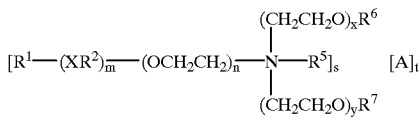

where $R^1$ is hydrogen or $C_{1-18}$ hydrocarbyl, each X is an ether, thioether, sulfoxide, ester, thioester or amide linkage, each $R^2$ is independently $C_{3-6}$ hydrocarbylidene, m is an average number of 0 to about 8, the total number J of carbon atoms in $R^1$—$(XR^2)_m$ is about 8 to about 24, n is an average number of 0 to about 5, $R^5$ is hydrogen, $C_{1-4}$ alkyl, an anionic oxide group or an anionic group —$(CH_2)_uC(O)O$ where u is 1 to 3, $R^6$ and $R^7$ are independently hydrogen or $C_{1-4}$ alkyl, x and y are average numbers such that x+y+n is not greater than a number E where E=25−J, A is an anionic entity and s is an integer from 1 to 3 and t is 0 or 1 such that electrical neutrality is maintained.

5. The composition of any of claims 1, 2 or 4 wherein said N-phosphonomethylglycine, predominantly in the form of the monoethanolammonium salt thereof, is in solution in the water in an amount of about 420 to about 570 grams of acid equivalent per liter of the composition.

6. The composition of any of claims 1, 2 or 4 wherein said N-phosphonomethylglycine, predominantly in the form of the monoethanolammonium salt thereof, is in solution in the water in an amount of about 480 to about 540 grams of acid equivalent per liter of the composition.

7. The composition of any of claims 1, 2 or 4 wherein the glyphosate concentration, expressed in g a.e./l, is higher than the maximum concentration that would provide acceptable storage-stability if all of the glyphosate were instead present as the isopropylammonium salt.

8. The composition of any of claims 1, 2 or 4 wherein the surfactant concentration, expressed in g/l, is higher than the maximum concentration that would be attainable if all of the glyphosate were instead present as the isopropylammonium salt.

9. The composition of any of claims 1, 2 or 4 having a viscosity less than an otherwise similar composition wherein all of the glyphosate is instead present as the isopropylammonium salt.

10. A herbicidal method comprising diluting in a suitable volume of water a herbicidally effective amount of a composition of any of claims 1, 2 or 4 to form an application composition, and applying the application composition to foliage of a plant or plants.

11. The composition of claim 4 wherein $R^1$ is a $C_{8-18}$ aliphatic, saturated or unsaturated, linear or branched hydrocarbyl chain and m is 0.

12. The composition of claim 4 wherein $R^1$ is a $C_{8-18}$ aliphatic, saturated or unsaturated, linear or branched hydrocarbyl chain, m is 1 to about 5, each —$XR^2$—group is a group —$OCH(CH_3)CH_2$—and n is 0.

13. The composition of claim 4 wherein $R^1$ is a $C_{8-18}$ aliphatic, saturated or unsaturated, linear or branched hydrocarbyl chain, m is 1, X is an ether linkage, $R^2$ is n-propylene and n is 0.

14. The composition of any of claims 11 to 13 wherein x and y are 0, $R^5$, $R^6$ and $R^7$ are independently $C_{1-4}$ alkyl and t is 1.

15. The composition of any of claims 11 to 13 wherein x+y is 2 or greater, $R^6$ and $R^7$ are hydrogen and t is 1.

16. The composition of any of claims 11 to 13 wherein $R^5$ is an anionic oxide group and t is 0.

17. The composition of any of claims 11 to 13 wherein $R^5$ is an anionic group —$CH_2C(O)O$, x and y are 0 and t is 0.

18. The composition of claim 4 wherein $R^1$ is a $C_{8-18}$ aliphatic, saturated or unsaturated, linear or branched hydrocarbyl chain, m is 1, X is an amide linkage, $R^2$ is n-propylene, n is 0, x and y are 0, $R^5$ is hydrogen or $C_{1-4}$ alkyl, $R^6$ and $R^7$ are independently $C_{1-4}$ alkyl and t is 1.

19. The composition of claim 4 wherein $R^1$ is hydrogen, m is about 3 to about 8, each —$XR^2$—group is a group —$OCH(CH_3)CH_2$—, x and y are 0, $R^5$, $R^6$ and $R^7$ are independently $C_{1-4}$ alkyl and t is 1.

20. The composition of claim 2 or claim 4 wherein A is chloride, bromide, iodide, sulfate, ethosulfate, phosphate, acetate, propionate, succinate, lactate, citrate, tartrate or an N-phosphonomethylglycine anion and t is 1.

* * * * *

UNITED STATES PATENT AND TRADEMARK OFFICE
CERTIFICATE OF CORRECTION

PATENT NO. : 6,277,788 B1
DATED : August 21, 2001
INVENTOR(S) : Daniel R. Wright It is certified that error appears in the above-identified patent and that said Letters Patent is hereby corrected as shown below:

Column 23,
Lines 65-66, delete "aromatic $C_{3-8}$ hydrocarbyl" and insert -- aromatic $C_{3-18}$ hydrocarbyl -- in place thereof.

Signed and Sealed this

Twenty-sixth Day of August, 2003

JAMES E. ROGAN
*Director of the United States Patent and Trademark Office*